United States Patent [19]

Dragisic et al.

[11] Patent Number: 5,065,757
[45] Date of Patent: Nov. 19, 1991

[54] SHIELDING TO PROTECT MATERIAL FROM LASER LIGHT

[76] Inventors: Branislav M. Dragisic, 700 Valley Rd., Itasca, Ill. 60143; Finley W. Markley, 918 Horne St., St. Charles, Ill. 60174

[21] Appl. No.: 194,315

[22] Filed: May 16, 1988

Related U.S. Application Data

[63] Continuation of Ser. No. 101,592, Sep. 28, 1987.

[51] Int. Cl.⁵ ............................................ A61M 16/00
[52] U.S. Cl. ............................ 128/207.14; 128/207.15
[58] Field of Search .................. 128/207.14, 207.15, 128/6, 303.1, 344; 138/138, 146, 127; 604/282; 250/515.1

[56] References Cited

U.S. PATENT DOCUMENTS

| | | | |
|---|---|---|---|
| 2,175,726 | 10/1939 | Gebauer | 138/127 |
| 2,210,744 | 8/1940 | Winder | 138/138 |
| 2,783,173 | 2/1957 | Walker et al. | 138/144 |
| 3,252,692 | 5/1966 | Langa | 250/515.1 |
| 3,684,605 | 8/1972 | Zwart | 604/282 |
| 4,081,647 | 3/1978 | Torrey | 219/10.55 D |
| 4,114,985 | 9/1978 | Friedman | 250/515.1 |
| 4,141,364 | 2/1979 | Schultze | 128/207.15 |
| 4,327,720 | 5/1982 | Bronson et al. | 128/207.15 |
| 4,375,811 | 5/1983 | Sabbota et al. | 604/97 |
| 4,378,796 | 4/1983 | Milhaud | 128/207.15 |
| 4,425,919 | 1/1984 | Alston, Jr. et al. | 604/282 |
| 4,489,722 | 12/1984 | Ferraro et al. | 128/207.15 |
| 4,520,814 | 6/1985 | Weeks | 128/303.1 |
| 4,547,193 | 10/1985 | Rydell | 138/127 |
| 4,558,093 | 12/1985 | Hatzenbuhler et al. | 128/207.15 |
| 4,604,998 | 8/1986 | Bellina | 128/849 |
| 4,611,588 | 9/1986 | Laptewicz, Jr. et al. | 128/207.15 |
| 4,616,641 | 10/1986 | Teeple | 128/303.1 |
| 4,632,108 | 12/1986 | Geil | 128/207.15 |
| 4,640,685 | 2/1987 | Croll | 250/515.1 |
| 4,650,287 | 3/1987 | Kudo et al. | 250/515.1 |
| 4,658,812 | 4/1987 | Hatzenbuhler et al. | 128/207.14 |
| 4,670,658 | 6/1987 | Meyers | 250/515.1 |
| 4,715,366 | 12/1987 | Teeple | 128/303.1 |
| 4,834,087 | 5/1989 | Coleman et al. | 128/207.14 |
| 4,847,506 | 7/1989 | Archer | 250/515.1 |
| 4,859,184 | 8/1989 | Hazard | 250/515.1 |
| 4,889,135 | 12/1989 | Poettgen | 250/515.1 |
| 4,901,738 | 2/1990 | Brink et al. | 606/2 |

OTHER PUBLICATIONS

The American Heritage Dictionary, 1982, p. 1313, 2nd Edition.

*Primary Examiner*—Edgar S. Burr
*Assistant Examiner*—Aaron J. Lewis
*Attorney, Agent, or Firm*—Wood, Phillips, Mason, Recktenwald & VanSanten

[57] ABSTRACT

A shield from a laser beam has an upper material which disperses the laser beam into a larger cross sectional area, and a lower material which reflects the dispersed laser beam back through the upper material. The upper material may be a woven fiberglass sheet and the lower material may be a sheet made of woven metallic wires. The shield may be made from cylindrical fiberglass and metallic fabric as a shield for an endotracheal tube for use during laser surgery of a patient's throat region. The materials may be made in sheets to form protective drapes for protection of equipment from a laser beam during laser surgery. An umbrella having a reflective surface that unfolds under pressure from a balloon used to secure an endotracheal tube in a patient's throat protects the balloon from the laser beam during laser surgery.

10 Claims, 5 Drawing Sheets

SHIELDING TO PROTECT MATERIAL FROM LASER LIGHT

CROSS-REFERENCE

This application is a continuation of application Ser. No. 101,592 filed Sept. 28, 1987 and entitled "Shielding To Protect Material From Laser Light."

FIELD OF THE INVENTION

The invention relates to shielding materials from laser light, and more particularly to shielding of an endotracheal tube and other medical equipment from laser light.

BACKGROUND OF THE INVENTION

During surgery it is often necessary to supply a stream of oxygen containing gas for the patient's lungs. An endotracheal tube is often found to be a convenient means for supplying a gas stream for the patient's lungs. An endotracheal tube is a tube through which anesthetic gases or vapors, as well as the respiratory gases, are conveyed into and out of the trachea. A standard form of endotracheal tube is made of plastic tubing and has an end inserted into the patient's trachea. A balloon is attached to the plastic tube near the end which is inserted into the patient's trachea, and a second tube is supplied for inflating the balloon. After the endotracheal tube is inserted into the patient's trachea, the balloon is inflated in order to seal the trachea so that the endotracheal tube is the only path for gas to enter and leave the patient's lungs.

When laser surgery is performed on the interior of the patient's throat, the plastic endotracheal tube presents a problem. Laser surgery usually employs a light source (the laser, and the light may be visible, infrared, or ultraviolet) to burn away tissue which the surgeon desires to remove. Also the laser light will burn a hole in the plastic endotracheal tube. A burn in the endotracheal tube may be dangerous for the patient for several reasons, including: the patient's supply of anesthetic gases and oxygen may be interrupted; the oxygen being delivered to the patient through the endotracheal tube may promote combustion causing the plastic endotracheal tube to flare into a flame; and smoke caused by the burn of the plastic tubing both may be toxic to the patient and may obstruct the surgeon's view of the patient's throat. A pressing problem in the field of laser throat surgery is to protect the endotracheal tube from the laser beam.

A shield for protecting an endotracheal tube from laser light has been disclosed, where the shield is made by mixing powdered metal with a plastic resin and applying the metalized resin to the surface of the plastic endotracheal tube, Ferraro et al. in U.S. Pat. No. 4,489,722 issued Dec. 25, 1984. Also a laser resistant material made by putting a dispersion of graphite powder in a polymer matrix is disclosed by Laptewicz, Jr. et al. in U.S. Pat. No. 4,611,588 issued Sept. 16, 1986. Also, protection of an endotracheal tube from laser light by flushing the volume enclosed by the patient's throat by using a stream of flowing nitrogen gas along with a metal shield to protect the balloon of the endotracheal tube is disclosed by Milhaud in U.S. Pat. No. 4,378,796 issued Apr. 5, 1983.

To be useful in practical surgery, a laser resistant endotracheal tube must have at least the following properties: be sufficiently flexible to conform to the shape of a patient's throat; be protected from rupture by heat from the laser beam; and produce a minimum of smoke when struck by the laser beam. Also, specular reflection of the laser beam from a metallic surface may cause the laser beam to reflect at nearly full intensity, strike the patient's tissue at an undesirable location, and cause an unwanted burn where the tissue is struck. The methods of protecting an endotracheal tube from laser light suggested in the prior art have not provided a satisfactory laser resistant endotracheal tube. Particularly, no adequate method of shielding the balloon of the endotracheal tube from laser light has been disclosed.

A further need in laser surgery is to have flat sheet laser resistant material in order to make drapes to protect equipment during laser surgery. For example, plastic tubing carrying gases or fluids to a patient are susceptible to rupture if they are struck by the laser beam. For example, during skin surgery it is possible for operating room equipment to be damaged by a misdirected laser beam.

Further, no satisfactory laser resistant flat sheet material suitable for making surgical drapes has been disclosed in the prior art. Aluminum foil or aluminum coated sheet plastic such as mylar have been tried, but have the disadvantage that a specular reflection of the laser beam can occur from the material. The reflected beam may not have its intensity sufficiently reduced, and therefore may be of sufficient intensity to damage equipment or injure personnel.

SUMMARY OF THE INVENTION

The invention is shielded material capable of protecting plastic medical equipment from a surgical laser. The material has a protective covering that is flexible, dissipates the heat delivered by a surgical laser beam so as to protect the material from being burned through by the laser, produces minimal smoke when struck by a surgical laser beam, and reflects only a small part of the light which strikes the material. A shielded material, where the material is susceptible to damage from a light beam, has an optically reflective and thermally conductive layer covering a portion of the material. A dispersive and absorptive layer capable of absorbing energy from the light beam covers the thermally conductive layer, and the thermally conductive layer conducts heat away from the absorptive layer. A plastic endotracheal tube is covered by a woven wire mesh cylinder, and a woven fiberglass cylindrical cloth covers the wire mesh. The woven wire mesh conducts heat and is flexible, and the fiberglass cloth absorbs and disperses the laser light. An umbrella made of a metal covered flexible material is folded to cover the balloon of an endotracheal tube before insertion of the endotracheal tube into the patient's trachea, and the umbrella expands with the balloon as the balloon is inflated. The umbrella is folded so that it collapses during withdrawal of the endotracheal tube after the balloon is deflated, and so causes only minimal injury to the trachea during withdrawal.

The laser resistant material is prepared in flat sheet form with a layer of optically reflective and thermally conductive material covered by a flat layer of an optically dispersive and absorptive material. The flat sheet material provides laser protected drapes to protect equipment and personnel during laser surgery.

Other and further aspects of the invention will become apparent by reference to the following drawings wherein like numerals designate like features in the several drawings.

DETAILED DESCRIPTION

Figure 1:
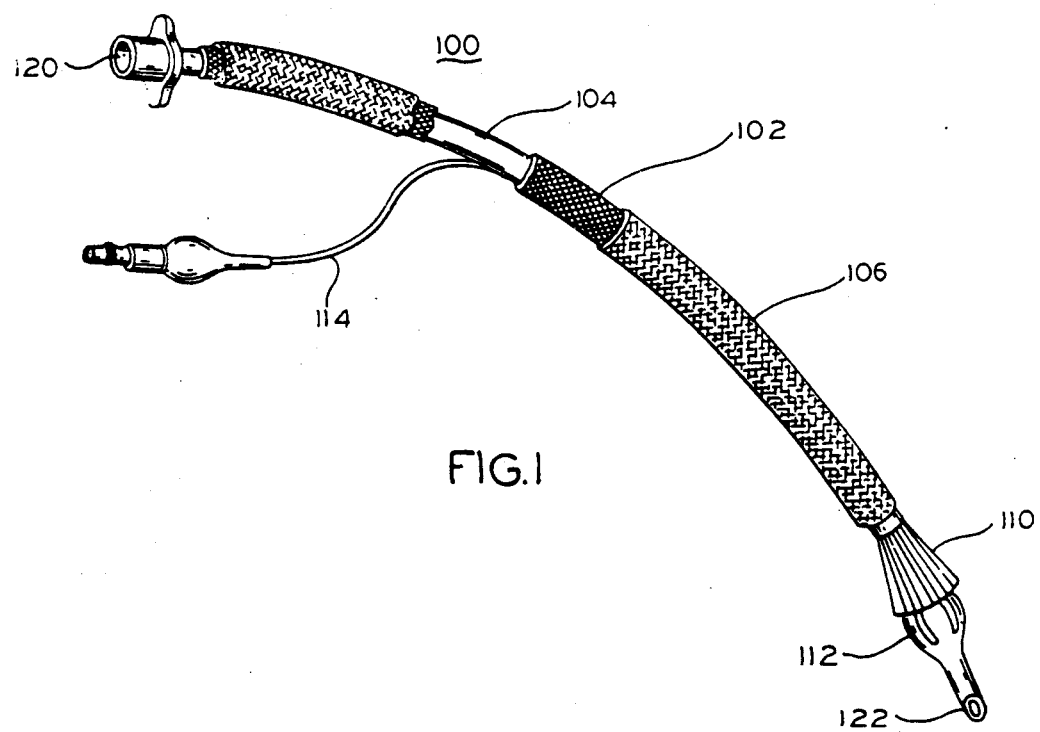
FIG. 1 is an isometric drawing of a shielded endotracheal tube.

FIG. 1 shows an endotracheal tube 100 protected against a laser beam (not shown). Woven metal fabric which is substantially continuous, tubular, thermally conductive and reflective 102 covers the plastic endotracheal tube 104. Woven fiberglass which is a diffusing layer 106 covers the woven metal fabric 102. Umbrella 110 is made of a flexible material covered by a metallic layer, and protects balloon 112 from a laser beam. Small tube 114 provides a conduit to balloon 112 for inflating balloon 112.

The woven metal fabric and the woven fiberglass materials disclosed herein may be made by several equivalent processes, as will be understood by those skilled in the art. For example, either the metal or the fiberglass material could be made by knitting, braiding, etc. It is to be understood that all materials equivalent to woven metal and woven fiberglass materials are referred to herein by the use of the expression "woven" material.

Figure 8:
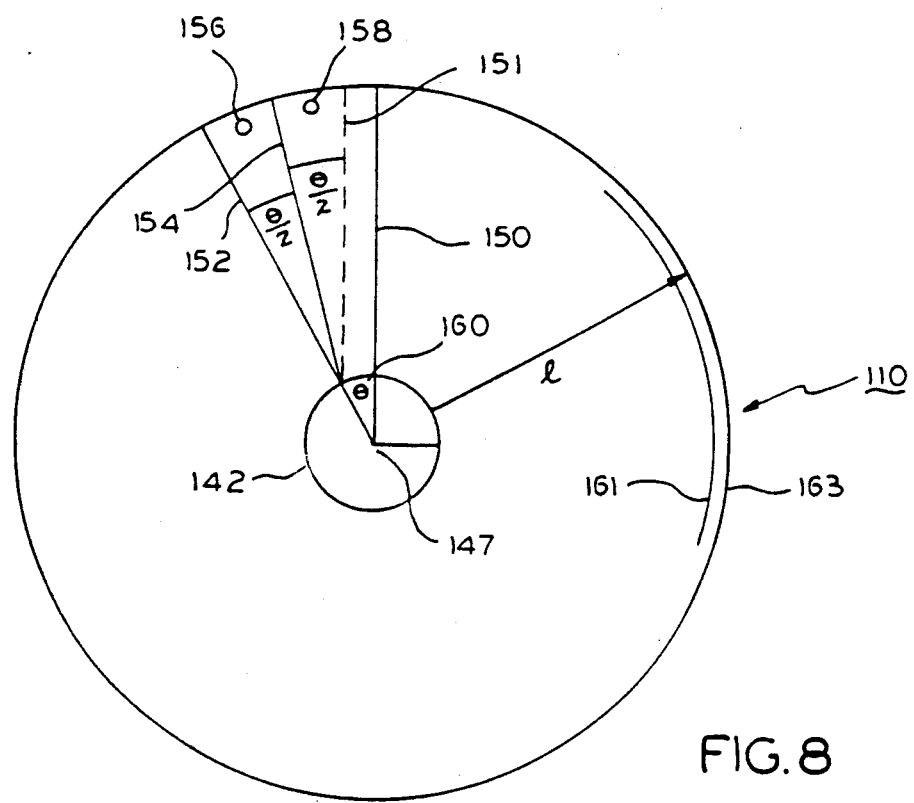
FIG. 8 is a detail view of an umbrella.
Figure 9:
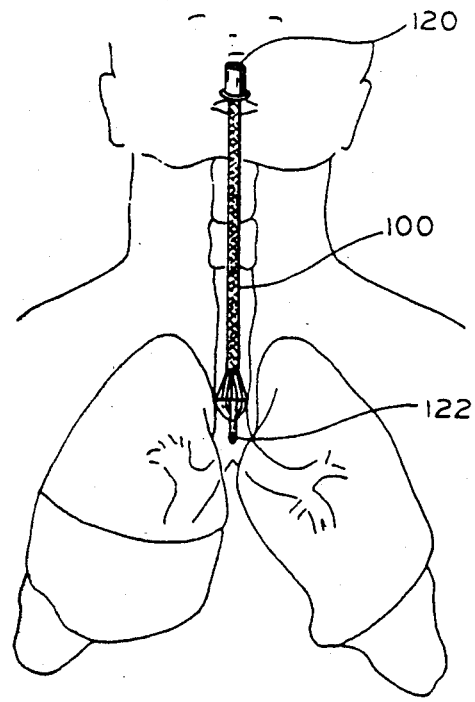
FIG. 9 is a front view showing a shielded endotracheal tube in place in a patient's trachea.
Figure 10:
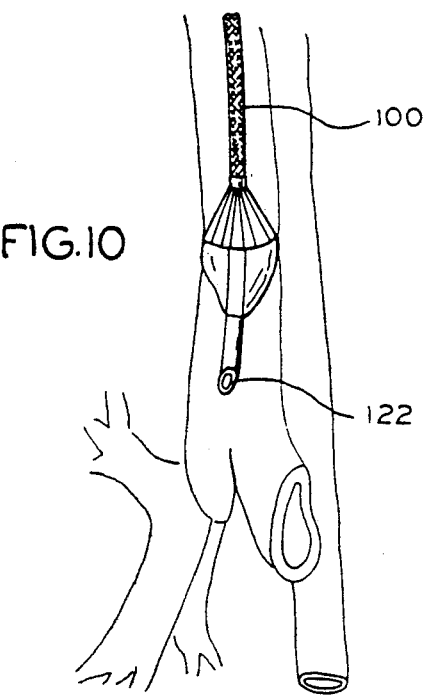
FIG. 10 is a detail view showing a shielded endotracheal tube in place in a patient's trachea.

Gases for the patient to breathe enter the endotracheal tube at opening 120 and exit from tube 104 at opening 122. After the endotracheal tube 100 is inserted in a patient's trachea, balloon 112 is inflated in order to seal the trachea so that the only conduit for gases to reach the patient's lungs is through tube 104. FIG. 8, FIG. 9, and FIG. 10 show endotracheal tube 100 in place in a patient's trachea.

Figure 2:
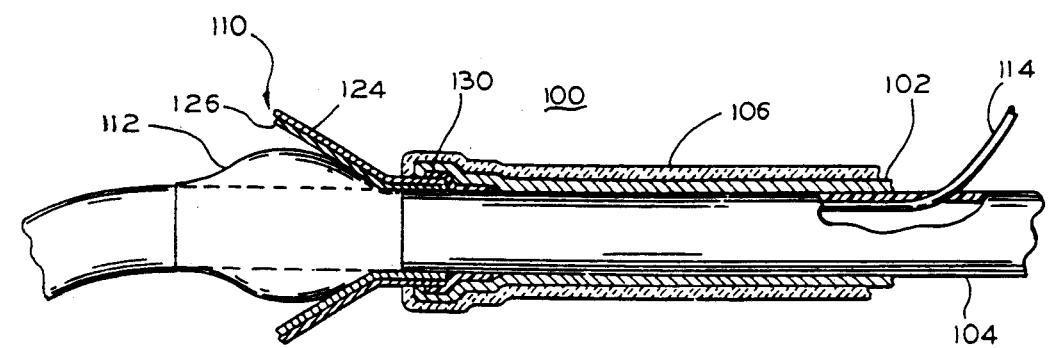
FIG. 2 is a cross sectional drawing of a shielded endotracheal tube.

FIG. 2 is a cross-section view showing endotracheal tube 100. Woven metallic material 102 is in the form of a cylindrical sleeve in contact with plastic tube 104. Woven fiberglass material 106 is in the form of a cylindrical sleeve in contact with metallic material 102. Umbrella 110 has a metallic layer 124 attached to a flexible material 126. Balloon 112 attaches to tube 104 beneath metallic material 102.

Figure 2A:
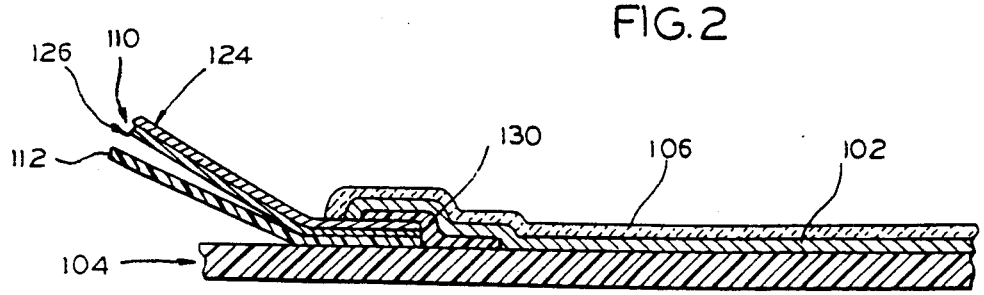
FIG. 2A is a detailed cross sectional drawing of a shielded endotracheal tube.

FIG. 2A is an expanded view of the cross section shown in FIG. 2. Tape 130 holds the attachment points of the umbrella in place. Umbrella 110 has a first open end directly adjacent flexible material 126 and second end fixedly mounted on tube 104 adjacent tape 130.

The use of material made from a woven structure such as small fiberglass threads is advantageous because the small diameter threads of glass refract the laser beam. The laser beam is able to cut tissue because it is focused to a small diameter and so delivers a lot of heat energy to a small volume of tissue. The small diameter glass threads of woven fiberglass serve to expand the diameter of the laser beam by each thread refracting the beam, and the layer of threads cumulatively expanding the light beam to a larger diameter. The larger diameter reduces the amount of heat that the beam delivers to a given area, and so reduces the intensity of the beam on the woven metal shield. The laser beam is reflected in various directions by the metal threads of the woven metal layer, thereby further spreading the diameter of the light beam. The reflected beam must then pass back through the woven fiberglass, during which passage the light beam is further spread into a larger diameter. Thus the light beam that is finally reflected from the two layer protective shield is spread out in diameter as well as being partially absorbed by the woven glass and woven metal, and so is reduced in intensity so that it does not cause burning of tissue when it inadvertently strikes tissue in undesired locations.

It has been found satisfactory to make woven metallic material 102 from the woven cylindrical shielding used in the construction of electrical co-axial cables. It has been found satisfactory to make woven fiberglass material 106 from cylindrical fiberglass tubing that is commercially available for insulating electrical wires that are at high temperature.

The endotracheal tube 100 is sufficiently flexible to conform to a patient's trachea when woven metallic fabric 103 is made of woven copper shielding material of the type used for shielding electrical co-axial cables, and fiberglass material 106 is made from commercially available woven fiberglass sleeving.

The inner layer of the endotracheal tube may be made of optically reflective and thermally conductive material with a high heat capacity, and an outer thermally resistant layer may be an optically transparent material having a high melting point. The thermally conductive layer is typically a metal subdivided to achieve suitable flexibility. As mentioned above, the thermally conductive layer may be a hollow tube of woven small diameter metal fibers such as the metal shielding commonly used on electric cables. The thermally resistant layer is typically glass or ceramic subdivided to achieve suitable flexibility and softness. As mentioned above, the thermally resistant material may be a hollow tube of very small diameter glass fibers such as the sleeves used to insulate electric wires at high temperatures.

The outer tube may be made of fiberglass or ceramic and consists of many very small transparent or translucent fibers. The outer tube therefore tends to disperse the laser beam by reflection and refraction. The laser beam is increased in diameter as it proceeds through the fiberglass layer so that the energy density is much less by the time that it strikes the metal layer. The metal layer is subdivided into many metal fibers, and so very little of the incident light is reflected directly backwards where it might impinge on the patient's tissues causing damage. The amount of laser light absorbed by the transparent or translucent fibers is not too large, thus preventing melting of the glass fibers.

When the dispersed laser beam hits the woven metal layer, it is further dispersed and reflected back towards its source. The beam must now traverse the fiberglass layer a second time, and is additionally dispersed and attenuated by it. Thus, any reflected laser light eventually reaching the patient's tissue is unlikely to be of sufficient intensity to cause damage.

The laser light absorbed in the fiberglass is unlikely to melt the fiberglass by the combined action of being dispersed so that the heating takes place over a relatively large volume, by the generated heat being conducted away by the metal underlayer, and by the high melting point of the glass fibers.

Additionally, the woven metal and woven glass layers may be saturated with sterile water or sterile saline solution, to increase the absorption of laser light, reduce the probability of any penetration of the metallic layer, and carry off some of the heat as water vapor.

The extremely small diameter of commercial grade glass fibers is advantageous for the action of the outer layer. The woven fiberglass tube can be very soft and non damaging to tissue of the trachea because of the small diameter of the glass fibers. The small diameter of the glass fibers also permits the weave of the fiberglass to be very tight and have high dispersion, and therefore to provide a very small probability of accidental penetration of the fiberglass by the direct laser beam.

The metal fibers commonly used to make commercially available woven metal tubing are of a larger diameter than the typical glass fiber, and therefore the resulting weave is not as tight as the fiberglass weave. Tests using only a woven metal tubing with no fiberglass outer layer showed occasional penetration through the interstices of the weave, and consequent damage to the inner plastic or rubber endotracheal tube.

Tests of a woven fiberglass layer alone showed melting and fraying of the fiberglass and eventual damage to the inner plastic or rubber endotracheal tube.

However, the combination of the inner woven metal tube and the outer fiberglass tube prevented damage to the rubber or plastic endotracheal tube. It was found during testing that even prolonged irradiation with a surgical carbon dioxide laser did not cause damage to the inner rubber or plastic tube. And damage did not occur even without wetting the tube with water.

It has been found that filling the interstices of the woven layers with silicone rubber was unsatisfactory because the laser light caused the silicone rubber to produce undesirable carbon particles.

It is desirable to impregnate the ends of the woven tubes with a binder to prevent fraying of the woven tubes at their ends. However, the binder may emit smoke when struck by a laser beam, and so the quantity of binder used must be kept to a minimum.

Alternatively, the woven tubes may be woven in place over the endotracheal tube.

The woven tubes may be slipped into place over the inner endotracheal tube. Or alternatively, the woven tubes may be woven in place over the inner endotracheal tube. In either case, fraying at the ends of the woven tubes must be kept to a minimum, and a small amount of binder may serve to reduce or eliminate fraying.

Figure 3:
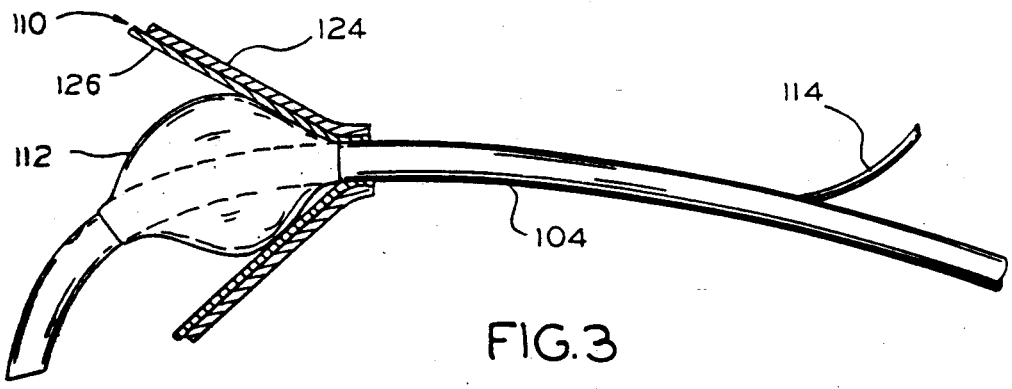
FIG. 3 is cross section drawing showing an umbrella protecting an inflated balloon of an endotracheal tube.

FIG. 3 shows a detail of umbrella 110 with balloon 112 in the inflated position. Metallic layer 124 is deposited on flexible material 126. It has been found satisfactory to make umbrella 110 from spun-bonded polypropylene paper-like material of the type used to make tear resistant envelopes. The metallic layer 124 may be satisfactorily made of aluminum foil covering a pressure sensitive adhesive layer, and the adhesive applied to the polypropylene paper-like layer 126. The surface of the metallic layer may advantageously be dulled, as by chemical etching, to reduce specular reflection of the laser light from the surface.

Figure 4:
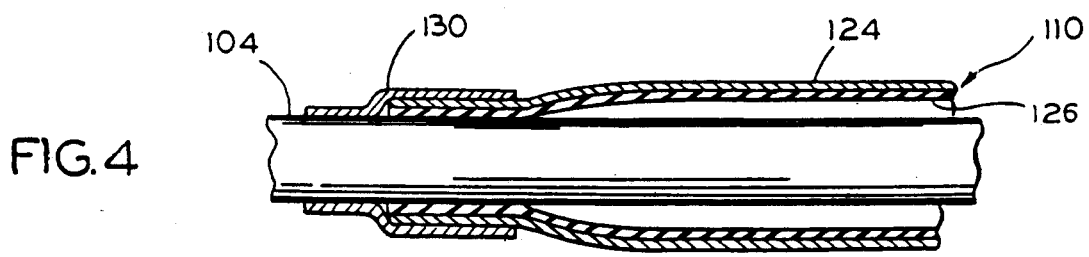
FIG. 4 is a cross section drawing showing attachment of an umbrella to an endotracheal tube.
Figure 5:
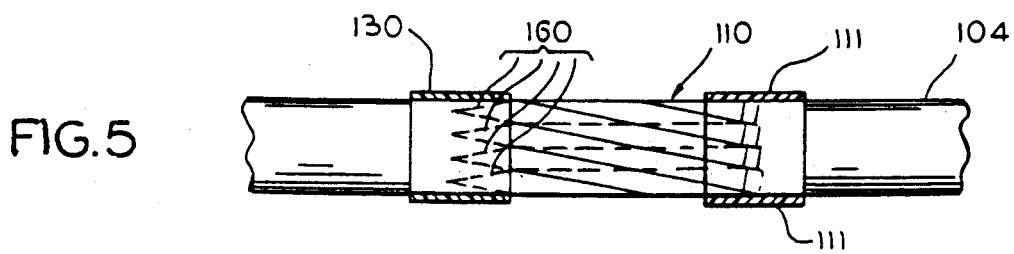
FIG. 5 is a side view showing attachment of an umbrella to an endotracheal tube.
Figure 6:
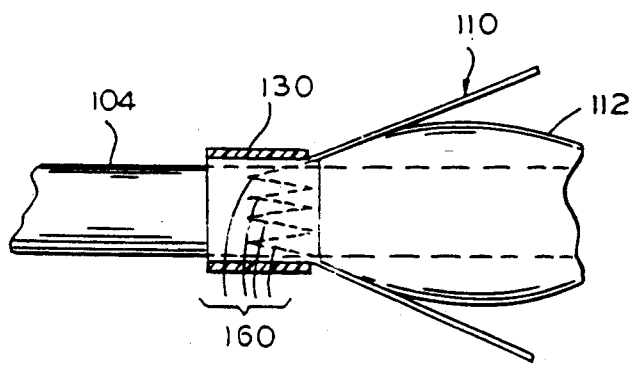
FIG. 6 is a side view showing an inflated balloon having an umbrella shield.

FIG. 4 is a detail cross section view of the attachment of umbrella 110 to tube 104. Tape 130 has a pressure sensitive surface which bonds umbrella 110 to tube 104. FIG. 5 is a side view of umbrella 110 in the folded position, and bonded to tube 104 by pressure sensitive adhesive tape 130. FIG. 6 shows balloon 112 in the inflated position. In FIG. 6, umbrella 110 has been raised into a conical shape by the expansion of balloon 112.

Points 160 provide a structure for attachment of umbrella 110 to a cylinder such as an endotracheal tube, as shown in FIGS. 5,6.

Figure 7:
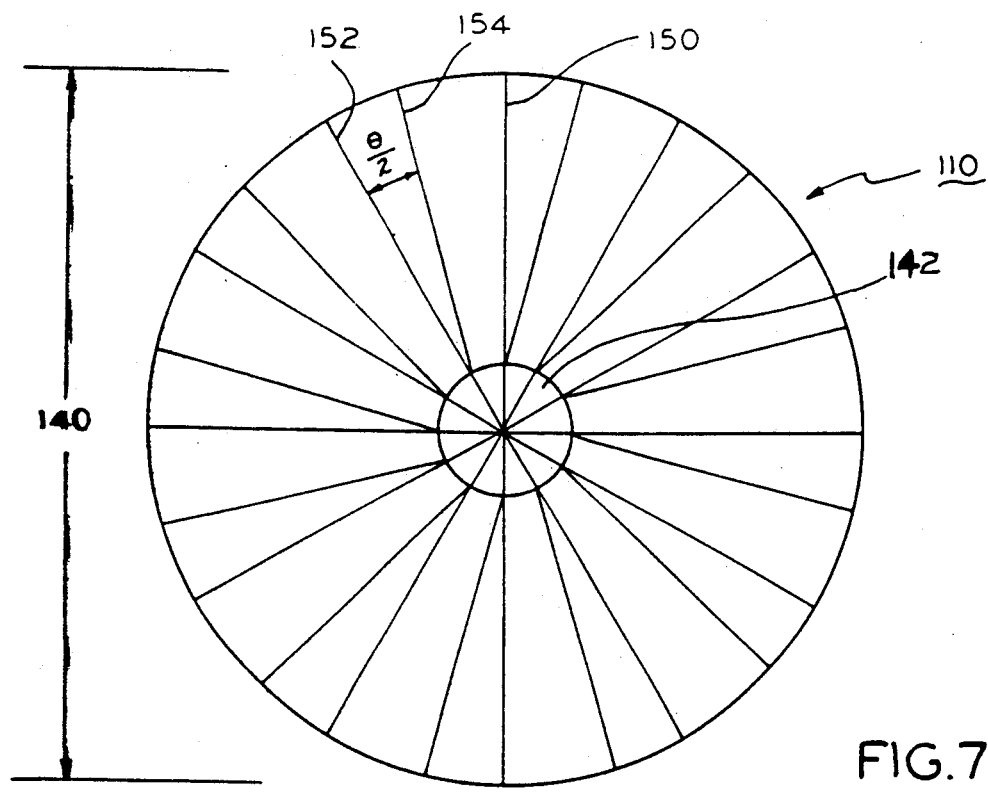
FIG. 7 is a detail view of an umbrella.
Figure 11:
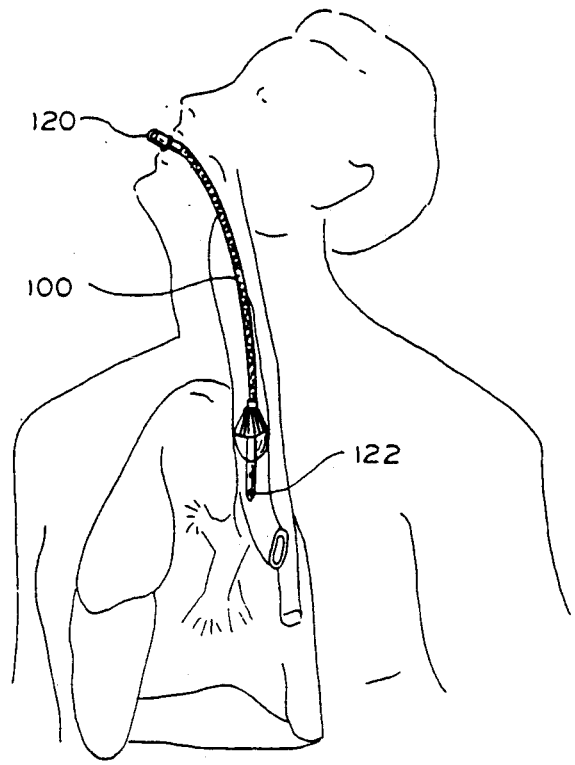
FIG. 11 is a side view showing a shielded endotracheal tube in place in a patient's trachea.

FIG. 7 is a detail view of umbrella 110. Umbrella 110 is cut out of a flat disc of material as shown in FIG. 7. The metallic layer 124 is scored along lines as shown in FIG. 7 in order that the material may be folded along the lines. Diameter 140 is chosen so that the edge of the umbrella 110 will fit within a patient's trachea, as shown in FIG. 9–FIG. 11. The diameter of opening 142 is chosen to fit snugly around the outer diameter of tube 104.

FIG. 8 gives a more detailed view of the scoring of the disc used to make umbrella 110. The disc has a center 147.

Line 150 is scored along a radius of the disc. Line 152 is scored along a radius of the disc. The diameter of opening 142 is chosen to snugly accommodate the outer diameter of tube 104. The angle (theta) between line 150 and line 152 is determined from the number of pleats that it is desired to have in umbrella 110, and is calculated as:

$$(theta) = 360/(number\ of\ pleats).$$

A fold line 154 is drawn at an angle of (theta)/2 from line 152, as shown in FIG. 8. An "out" fold is made along line 152, an "in" fold is made along line 154, and another "out" fold is made along line 150. After folding, spot 156 touches spot 158, and a drop of adhesive is applied to hold spot 156 in contact with spot 158. Inside opening 142, cuts are made along both lines 150 and 152 to form triangular regions such as triangular region 160. A sequence of score lines such as lines 150, 152, 154 are made at angles of (theta) around the disc, as shown in more detail in FIG. 7. As shown in FIG. 5 and FIG. 6, triangular regions 160 provide the attachment means for attaching umbrella 110 to tube 104.

An alternative to using a drop of adhesive to hold spot 156 in contact with spot 158 is shown in FIG. 5 as resilient band 111. Resilient band 111 has sufficient width to overlap both a portion of endotracheal tube 104 and the edge of umbrella 110. Resilient band 111 is attached to endotracheal tube 104 by, for example, heat sealing, solvent bonding, or other suitable means. As balloon 112 inflates it causes the edge of umbrella 110 to press outwardly against resilient band 111, thereby deforming resilient band 111 so that the edge of umbrella 110 comes free of resilient band 111. Resilient band 111 may be made of thin sheet vinyl so that it will deform under pressure resulting from inflation of balloon 112, or, for example, resilient band 111 may be made from a thin rubber material that does not deform permanently after the edge of umbrella comes free from resilient band 111.

Circular line 161 is a radius drawn about center 147. Circular line Circular line 161 marks the extent of covering of the material by the metallic layer. The circular ring of material between radius 161 and radius 163 is therefore free of metallic covering. The uncovered material between radii 161, 163 presents a soft edge to the tissue of the patient's trachea, and therefore reduces the chance of injury to the tissue of the throat and trachea by cutting with the metallic layer.

The inflatable balloon at the end of the endotracheal tube is protected from the laser light by a disc of material that is folded into a cylindrical shape, the umbrella. The cylindrical shape covers the balloon as the endotracheal tube is inserted into the patient's trachea. When the balloon inflates, the cylinder partially unfolds into a conical shape. The outer edge of the conical shape contacts the tracheal wall, thus blocking laser light from striking the balloon. The material used must be readily folded and creased without tearing. A spunbonded polypropylene paper-like material has been found to be satisfactory. The paper-like material is covered by a metallic layer. A commercially available aluminum foil covered pressure sensitive tape has been found to be a suitable material. The pressure sensitive tape bonds the aluminum foil covering to the polypropylene paper-like material.

It is desirable to dull the surface of the aluminum foil so as to disperse a specular reflection. It is desirable to disperse a specular reflection so that the intensity of the reflected light beam is attenuated, thereby protecting tissue from being burned by the reflected light beam.

The diameter of the aluminum foil is advantageously less than the diameter of the polypropylene disc so that the end of the unfolded cone shape contacting the trachea is non-metallic and thus softer and less likely to irritate the tissue.

When folded into its cylindrical form the downstream edges of each fold are lightly bonded to the adjacent underlying fold. The bonding can be with, for example, a silicone rubber adhesive. This slight attachment at the corner of each fold prevents the cylinder from unfolding when the endotracheal tube is inserted into the trachea. When the balloon is inflated, these corner adhesive bonds are easily broken, thereby allowing the cylinder to expand into a cone shape. On extraction from the trachea, the cone shape tends to naturally fold back into its cylindrical form and so causes very little injury to the tissue of the trachea.

Figure 12:
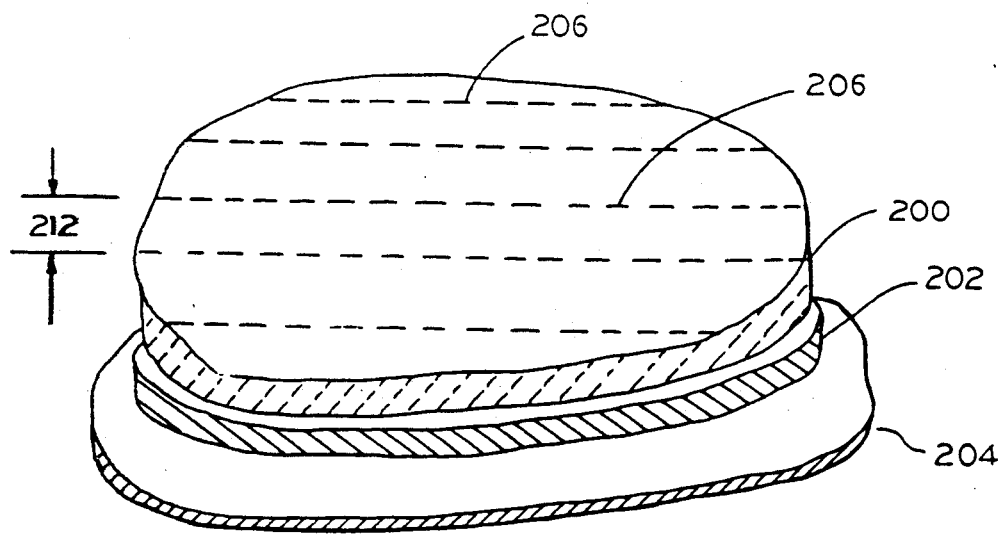
FIG. 12 is an isometric view of flat sheet shielded material.

FIG. 12 shows an isometric view of shielded material having a flat sheet shape. The material shown in FIG. 12 is suitable, for example, for use as drapes in protecting equipment used in an operating room from a surgical laser beam. An upper layer 200 is made of flat sheet woven fiberglass. A metallic layer 202 is made of woven metal fibers. A backing layer 204 is made of flexible material to provide support for layers 200, 202. Stitches 206 hold the layers together. Stitches 206 may be made of thread such as cloth, nylon, or other hydrocarbon fiber. Or alternatively, stitches 206 may be made of fiberglass. The criticality of preventing smoke of a particular application determines the choice of material for the stitches 206.

In some applications, backing layer 204 may not be necessary. For example, if a sheet of fiberglass sewn to a sheet of metallic cloth is sufficiently strong for a particular application, then it may be possible to eliminate backing layer 204. On the other hand, in some applications, it may be desirable to use spun bonded polypropylene for backing layer 204. Also, backing layer 204 could be made of paper or cloth, depending upon the application.

Metallic layer 202 may be made of woven metallic fiber, as mentioned above, or may alternatively be made of, for example, metallic foil such as aluminum foil, or, for example may be made of a metallic deposit on a sheet such as sheet plastic or mylar.

Figure 13:
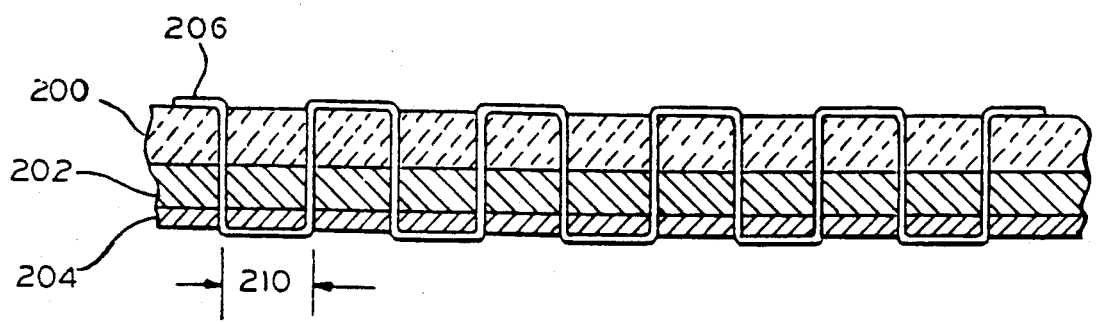
FIG. 13 is a cross sectional view of flat sheet shielded material.

FIG. 13 is a cross sectional view showing flat sheet laser light resistant material. Stitches 206 hold woven fiberglass layer 200, metallic layer 202, and backing layer 204 together. The stitches 206 may be sewn into place using a sewing machine. The pitch 210 of the stitches and the spacing 212 (shown in FIG. 12) of the stitches is selected to achieve a tight fit between the woven fiberglass layer 200 and the metallic layer 202.

Alternatively, an interlocking stitch (not shown) using two threads may be used, wherein two threads interlock within the materials.

Figure 14:
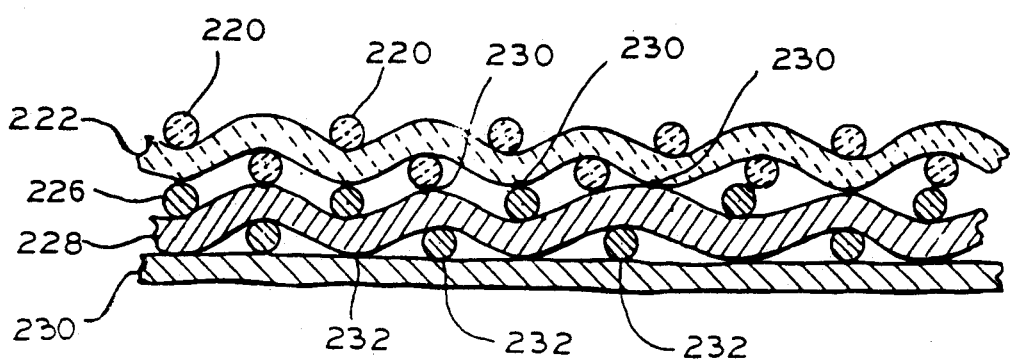
FIG. 14 is a cross sectional view of flat sheet shielded material.

FIG. 14 is a cross section view showing an alternative method of bonding between the woven fiberglass layer and a woven metallic layer. Fiberglass fibers 220 are oriented at right angles to the cross section of FIG. 14, while fiberglass fiber 222 is parallel to the cross section of FIG. 14. Metallic fiber 226 is perpendicular to the cross section of FIG. 14, while metallic fiber 228 is parallel to the cross section of FIG. 14. Glue spots 230 bond the fiberglass fibers to the metal fibers. Glue spots 232 bond the metallic fibers to the backing material 230. Most glue materials contain hydrocarbon materials and so tend to emit smoke when heated by a laser beam. However, many applications such as protective drapes for operating room equipment may permit the emission of smoke from the drapes without any harmful effects from the smoke.

The amount of glue applied to the woven materials to form glue spots 230, 232 may be minimized by use of a rigid roller to apply the glue. A minimum amount of glue will make a minimum amount of smoke when heated by the laser beam. A rigid roller having a thin layer of glue spread thereupon will tend to put the majority of the applied glue on the high spots of the woven material. Thus the woven layers will be bonded mainly at their respective high spots. Having spots of glue only at the high spots minimizes the amount of glue applied.

MANUFACTURE OF A LASER RESISTANCE ENDOTRACHEAL TUBE

A laser resistant endotracheal tube may be manufactured as follows. First, manufacture a balloon shield, a woven metal tube, and a woven fiberglass tube. Second, slide the balloon shield over the inner plastic endotracheal tube until it is in position over the balloon with the attachment points lying on the tube just upstream from the balloon. Third, attach the shield points with adhesive or pressure-sensitive tape to the tube. Fourth, slide the woven metal tube over the inner plastic endotracheal tube and cover the points of the balloon shield. Fifth, slide the woven fiberglass tube over the woven metal tube so that the fiberglass tube just covers the woven metal tube. Sixth, bond the corners of the folds of the balloon shield to each other to prevent accidental opening of the shield during insertion of the endotracheal tube into the patient's trachea.

To manufacture the balloon shield the following steps have been found to be satisfactory. First, sodium hydroxide etch a pressure sensitive aluminum foil tape, wash it and dry it. Second, apply the tape to a spunbonded polypropylene paper. Third, die cut the foil and paper into a disc with an outer diameter between approximately 1.5 to 2 times the inner diameter expected for a patient's trachea. Fourth, cut the central portion into pie shaped points to a diameter approximately equal to the outer diameter of the plastic inner endotracheal tube. Fifth, cut the aluminum foil and crease the paper along the fold lines. Sixth, fold the shield into a cylinder.

Woven tubes of metal fibers and of fiberglass fiber may be manufactured and assembled according to the following steps. First, obtain tubes of the desired material which have been woven on a commercial weaving machine, and cut the tubes into long lengths. Second, compress the tube axially to increase its diameter so that it may be slid over a mandrel of the correct diameter. It has been found advantageous to cover the mandrel with polytetrafluorethylene to provide low friction and prevent adhesion. Third, pull the tube tight on the mandrel and apply a ring of room temperature curing silicone rubber around the tube at intervals of the desired final length. The silicone rubber may emit smoke if the silicone rubber is struck by a laser beam, and for this reason the amount of silicone rubber used should be kept to a minimum consistent with preventing the ends of the threads from unravelling. Fourth, when the silicone rubber has cured, slip the tube off the mandrel and cut to desired lengths through the cured silicone rubber in order to prevent fraying of the cut. The fiberglass tube may be formed over the woven metal tube while the woven metal tube is on the mandrel, and the two assembled as one over the inner plastic endotracheal tube. Or the woven metal tube may be first slipped over the inner plastic endotracheal tube and the fiberglass tube later assembled over the woven metal tube. Fifth, when the tubes are in place over the endotracheal tube they can be pulled tight in order to make them fit tightly over the plastic inner endotracheal tube so that they will not slip.

While only certain preferred features of the invention have been shown by way of illustration, many modifications and changes will occur to those skilled in the art. It is, therefore, to be understood that the appended claims are intended to cover all such modifications and changes as fall within the true spirit and scope of the invention.

What is claimed is:

1. An endotracheal tube comprising:
   a tube capable of supplying gas to a patient;
   means for protecting said tube from damage by light from a laser, said means including a woven metal shield encircling at least a portion of said tube;
   a woven fiberglass shield encircling said woven metal shield;
   said woven metal shield and said woven fiberglass shield constituting means for reflecting light from a laser and means for dispersing light from a laser, respectively.

2. An endotracheal tube as in claim 1 further comprising:
   a balloon connected to said endotracheal tube near an end thereof and inflatable oppositely of said end to secure said endotracheal tube in said patient's trachea;
   an umbrella, secured to said endotracheal tube adjacent said balloon and being folded to cover said balloon during insertion of said endotracheal tube into said patients' trachea, and said umbrella opening to shield said balloon from said laser light as said balloon is inflated.

3. An endotracheal tube, comprising:
   a tube capable of supplying gas to a patient's lungs;
   a collapsed balloon mounted on said tube near an end thereof and inflatable to secure said tracheal tube in said patient's trachea; and
   an umbrella having a first open end free to move in response to inflation of said balloon and a second end mounted on said tube adjacent to said balloon and oppositely of said tube end said umbrella being folded over said balloon to cover said balloon during insertion of said endotracheal tube into said patient's trachea, said umbrella opening to shield said balloon from laser light responsive to inflation of said balloon.

4. An endotracheal tube as in claim 3 wherein said umbrella is made of a flexible material having a flexible metal coating attached thereto.

5. An endotracheal tube as in claim 4 wherein said metal coating has its surface dulled so as to reduce the intensity of light reflecting from said metal layer.

6. An endotracheal tube comprising:
   a plastic tube capable of supplying gas to a patient and formed of a material that will melt and/or oxidize and/or vaporize when struck by the beam of a laser;
   means for protecting said tube from damage by light from laser including a first substantially continuous thermally conductive and reflective tubular layer surrounding said tube along the length thereof and formed of a material that is both thermally conductive as well as reflective of laser light; and
   a second tubular diffusing layer surrounding said thermally conductive and reflective tubular layer oppositely of said tube and formed of a transparent material constructed to diffuse a beam of laser light impinging on said diffusing layer and having an exposed surface opposite of said thermally conductive and reflective layer that may be exposed to a beam of laser light.

7. The endotracheal tube of claim 6 wherein said thermally conductive and reflective layer is formed of metallic filaments.

8. The endotracheal tube of claim 6 wherein said diffusing layer is made up of glass-like filaments.

9. The endotracheal tube of claim 6 wherein said thermally conductive and reflective layer is formed of woven metallic filaments and said diffusing layer is made up of woven glass fibers.

10. The endotracheal tube of claim 6 further including a collapsed balloon mounted on said tube near an end thereof, means for selectively inflating said balloon, a collapsed umbrella-like shield mounted on said tube adjacent to said balloon on the side thereof opposite said tube end and having a free edge folded over said balloon, said collapsed shield being responsive to inflation of said balloon to cause said free end to spread to shield said balloon from laser light.

* * * * *